United States Patent [19]

Havstad

[11] 4,151,740
[45] May 1, 1979

[54] SILICON NITRIDE LIFE PREDICTION METHOD

[75] Inventor: Peter H. Havstad, Livonia, Mich.

[73] Assignee: Ford Motor Company, Dearborn, Mich.

[21] Appl. No.: 926,609

[22] Filed: Jul. 21, 1978

[51] Int. Cl.² ............................................. G01N 25/00
[52] U.S. Cl. ..................................................... 73/15 B
[58] Field of Search ...................... 73/15 R, 15 B, 116, 73/119 R

[56] References Cited

U.S. PATENT DOCUMENTS

| | | | |
|---|---|---|---|
| 3,292,417 | 12/1966 | Hayden et al. | 73/15 |
| 3,357,239 | 12/1967 | Hohenberg | 73/116 |
| 3,950,985 | 4/1976 | Buchwald | 73/116 |

Primary Examiner—Herbert Goldstein
Attorney, Agent, or Firm—Keith L. Zerschling; William E. Johnson

[57] ABSTRACT

A method is disclosed for predicting the service life of silicon nitride material under operating conditions of a ceramic turbine engine in whch an article is subjected to high temperatures under oxidizing conditions. The method for selecting a silicon nitride article to be used under these high temperature oxidizing conditions is generally as follows.

A determination is made of the weight gain of a silicon nitride article under oxidizing conditions for a testing period of at least 12 hours at a temperature in the range from about 1800° F. (932° C.) to about 2500° F. (1371° C.). The weight gain determination is made after the silicon nitride article has been manufactured, and prior to its being subjected to any previous high temperature oxidizing conditions. The weight the silicon nitride article would gain at a projected time, which is a number of hours greater than the testing period, is empirically determined from the weight gain determinations made in the testing period. The silicon nitride article is accepted or rejected for further use under high temperature oxidizing conditions based upon the empirically determined weight gain at the projected time. For example, if the amount of weight gained at the projected time is too great, the article is rejected as being one which will not have a long life under high temperature oxidizing conditions.

4 Claims, 3 Drawing Figures

Screening For Life Capability

Weight Gain vs Time Data

Identification Of $Si_3N_4$ Failures

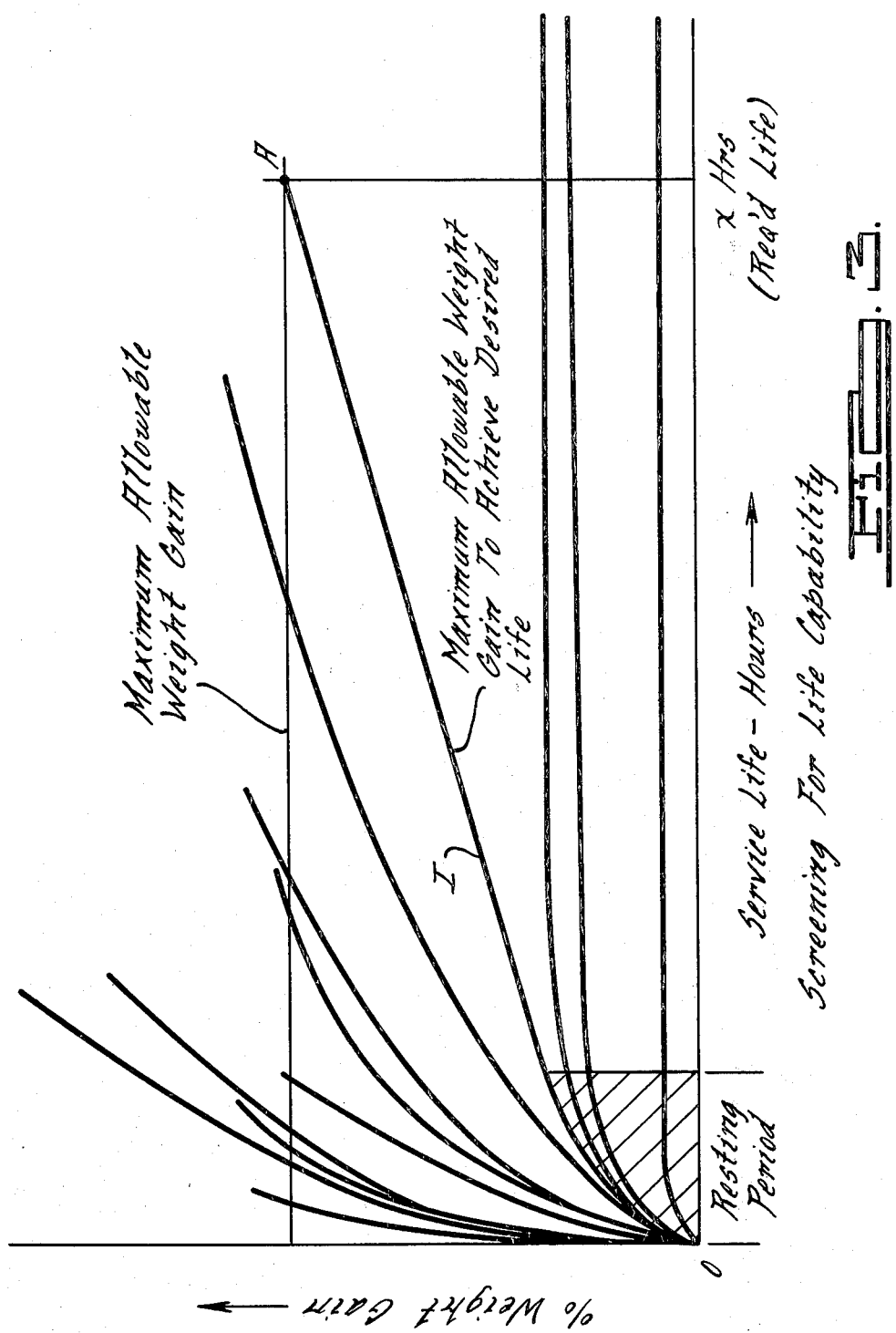

SILICON NITRIDE LIFE PREDICTION METHOD

This application results from development work carried out for the Department of the Army under Contract No. DAAG-46-71-C-0162.

BACKGROUND OF THE INVENTION AND PRIOR ART STATEMENT

The applicant is unaware of any method by which one could predict the useful life of a silicon nitride article under high temperature oxidizing conditions prior to the method developed by him.

A novelty study conducted in the files of the U.S. Patent Office by a search firm resulted in the citation of no prior art considered relevant by the search firm.

SUMMARY OF THE INVENTION

This invention relates to a method for predicting the useful life of a silicon nitride article under high temperature oxidizing conditions. This method permits one to manufacture a plurality of silicon nitride articles, test the same in accordance with the procedure of this method, and thereafter select those manufactured articles which will have a relatively long and useful life under high temperature oxidizing conditions. The method of this invention is based upon the discovery that weight gained by a silicon nitride article under high temperature oxidizing conditions in a testing period after the manufacture of the articles is a key which indicates the useful service life that one may expect from that article in further running under high temperature oxidizing conditions.

In accordance with the broad principles of the method of this invention, a method of selecting a silicon nitride article for use under high temperature oxidizing conditions is as follows. A silicon nitride article is manufactured and the weight gain of that silicon nitride article under oxidizing conditions is determined for a testing period. The testing period lasts at least 12 hours and is conducted at a temperature in the range from about 1800° F. (932° C.) to about 2500° F. (1371° C.). The weight the silicon nitride article would gain at a projected time, which is a number of hours greater than the testing period, is empirically determined from the weight gain determinations in the testing period. The silicon nitride article is accepted or rejected for further use under high temperature oxidizing conditions based upon the empirically determined weight gain at the projected time. In this manner, the silicon nitride articles which will have a useful service life may be sorted out and used while those silicon nitride articles which will have an unacceptable life under high temperature oxidizing conditions can be discarded prior to their use.

In accordance with a preferred embodiment of this invention, a method of predicting the service life of a silicon nitride article is as follows. A silicon nitride article is formed and weighed to obtain its initial weight. The silicon nitride article is heated in an oxidizing ambient to an aging temperature in the range from about 1800° F. (932° C.) to about 2500° F. (1371° C.). The silicon nitride article is maintained at the aging temperature for a total of at least 12 hours to establish a testing period. The silicon nitride article is cooled back to room temperature (a) at least twice during the period of time over which the testing period is being established, and (b) also at the end of the testing period. The silicon nitride article is weighed each time it is cooled back to room temperature to obtain the weight gain by the silicon nitride article.

A function of the weight gain of the silicon nitride article is plotted versus a function of the amount of time elapsed in the testing period at which the weight gain was measured. A curve is fitted through the plotted data. This curve is extrapolated into an area of the graph representing an extended period of time. The projected service life of the silicon nitride article is determined from the extrapolated curve at the extended period of time.

The method of this invention will be understood in greater clarity after one has read the remaining portion of this specification, particularly when studied in conjunction with the material graphically depicted in FIGS. 1 through 3 associated therewith.

BRIEF DESCRIPTION OF THE DRAWINGS

FIG. 3 is a graphical depiction of the data of FIG. 1 showing a overlie identifying how one ascertains whether a tested article will have the desired service life from test data developed in a short testing period.

DESCRIPTION OF THE PREFERRED EMBODIMENT

In accordance with the broad principles of this invention, a method of selecting a silicon nitride article for use under high temperature oxidizing conditions is disclosed. The method is carried out on newly formed silicon nitride articles in the following manner. Each silicon nitride article is subjected to oxidizing conditions for a testing period of at least 12 hours at a temperature in the range from about 1800° F. (932° C.) to about 2500° F. (1371° C.). During this testing period, the weight gain of the silicon nitride article is determined. The weight the silicon nitride article would gain at a projected time which is a number of hours greater than the testing period, is empirically determined from the weight gain determinations made in the testing period. The silicon nitride article is accepted or rejected for further use under high temperature oxidizing conditions based upon the empirically determined weight gain at the projected time.

Figure 1:
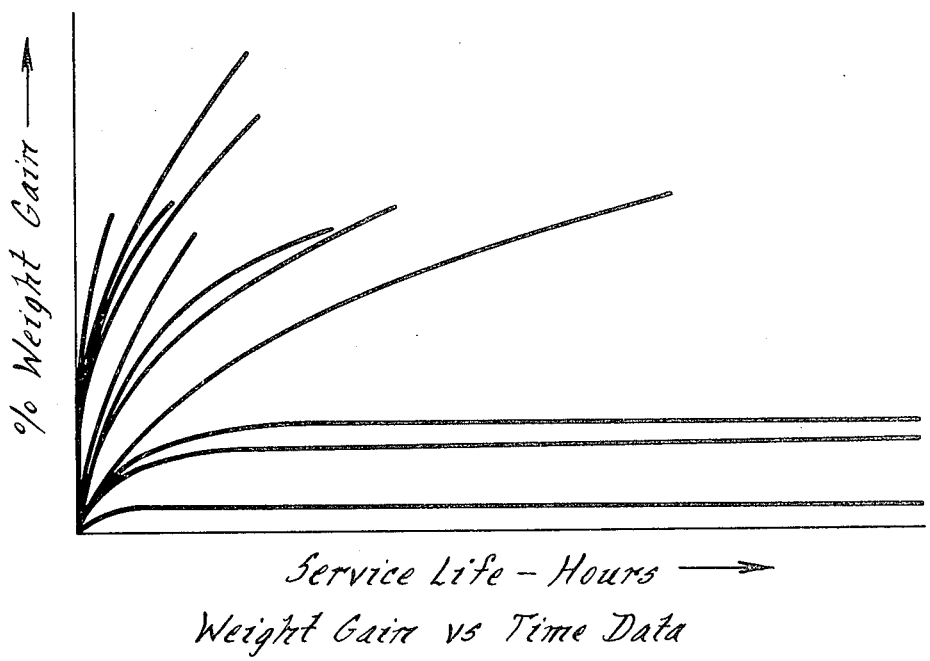
FIG. 1 is a graphical depiction of weight gain versus time data for a number of silicon nitride articles.
Figure 2:
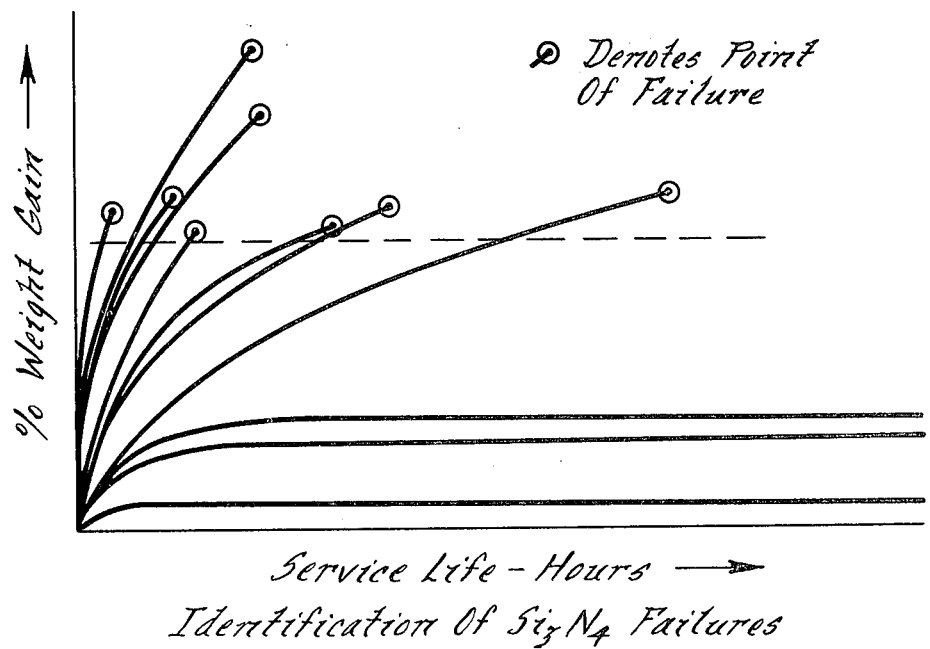
FIG. 2 is a graphical identification of silicon nitride article failures which occurred on the articles whose data was plotted in FIG. 1.

In order to understand the broad principles of this invention as discussed immediately above, reference is made to the FIGS. 1 through 3 of the drawings.

In FIG. 1, a graphical presentation is made with respect to a number of silicon nitride articles which have been tested by me. Each of the silicon nitride articles is identified by a curved line in FIG. 1 which depicts the percent weight gained by that article as a function of the time that article was tested under a high temperature oxidizing condition. In particular, I ran a number of such articles and plotted the data therefrom, namely, the percent weight gain of each article versus the service life or testing time of the article.

The articles were all tested under oxidizing conditions at a temperature in the range from about 1800° F. (932° C.) to about 2500° F. (1371° C.). When it was desired to weigh the articles in order to determine the percentage of weight gain, the articles were cooled to room temperature. The testing time does not count the periods of time during which the articles were cooled back to room temperature for the purpose of weighing the same and then reheated to the testing temperature. Normally, the cooling and reheating do not have to be controlled at any particular rate. The percentage weight gain, of course, is easily determined. One needs know only the weight of the original article and the weight of that article at the particular time that the test has been interrupted in order to ascertain the percent weight gain.

In all of the graphical presentations, the two functions plotted are the service life in hours and the percent weight gained by the article. Other functions of these variables could also be plotted to produce graphical presentations of the data. However, I have found that the present weight gain versus service life in hours is a very good set of functions to choose for the graphical presentation.

FIG. 2 is a graphical presentation of the percent weight gain versus service life in hours of several silicon nitride articles, some of which failed under testing conditions. By failure, I mean that the articles cracked and broke down. Such failures are indicated by the circles drawn in the graphical presentation. It is apparent that all of the failures have occurred above a certain percentage weight gain. In the manner in which I have presented the data in FIG. 2, the failures generally occur at a point above two percent by weight gain.

It occurred to me that there was then, in fact, a relationship between the weight gained by a silicon nitride article and the time in which that weight was gained over a testing period. It, therefore, appeared that one was able to develop a method to test silicon nitride articles in order to ascertain whether or not they would have a prolonged life.

I found that I could conduct a testing period on each silicon nitride article and determine from that testing period the weight gain of the silicon nitride article. The testing periods were carried on under oxidizing conditions at a temperature in the range from about 1800° F. (932° C.) to about 2500° F. (1371° C.). The testing period was for a period of time of at least 12 hours, preferably 16 hours, and generally no more than 20 hours. The weight gain of the article was measured at intervals of time during the test period. The number of times that could be used generally was at least two in number during the test period, with a third reading coming at the end of the test period. For example, if a 16 hour testing period was chosen, other readings were taken for weight gain at the fifth and tenth hours of the test. In order to take readings of weight gain, it is necessary to cool the article back to room temperature. As aforementioned, the cooling and reheating of the article from the test temperature is not taken into account for the time of the service life in hours. This cooling and reheating time is excluded from the testing period.

The data of weight gain versus service life is plotted as per FIG. 3 and an empirical determination is made of the weight the silicon nitride article would gain at a projected time from the plotted data. For example, with reference to FIG. 3, if the data was plotted and it formed along the maximum allowable weight gain curve identified with the numeral I, it would have a service life indicated at X hours. Any data plotted in the testing period which generated a curve falling below the one identified with the numeral I, would have a longer service life than X hours. Thus, by taking the data plotted in the testing period and by extrapolating that data outwardly into an extended service life hours condition, one is able to ascertain the desired or useful life that can be obtained from that article. If the extrapolated data falls above the curve identified by the numeral I in FIG. 3, the service life in hours is generally too low to make the part have any useful value under service conditions.

Therefore, in accordance with the teachings of the detailed method of this invention, a method of predicating the service life of a silicon nitride article is as follows. A silicon nitride article is formed and weighed to obtain its initial weight. The silicon nitride article is heated in an oxidizing ambient to an aging temperature in the range of about 1800° F. (932° C.) to about 2500° F. (1371° C.). The silicon nitride article is maintained at the aging temperature a total of at least 12 hours to establish a testing period. Preferably, this testing period is about 16 hours, and generally should not exceed about 20 hours, as that much testing or more is not required and is simply a waste of effort. The silicon nitride article is cooled back to room temperature (a) at least twice during the period of time over which the testing period is established, and (b) also at least at the end of the testing period. The article may be cooled back more than twice during the testing period if one desires to do so, but generally only three data points are necessary to establish readings in this case. The time of cooling and reheating of the article does not count towards the time of the testing period.

The silicon nitride article is weighed each time it is cooled back to room temperature to obtain the weight gained by the silicon nitride article. That weight gain is correlated with the time of the testing period and the function of the weight gain is plotted versus a function of the amount of time elapsed in the testing period at which the weight gain was measured.

A curve is fitted through the plotted data, which in FIG. 3 would cover data plotted during the testing period. That curve is then extrapolated into an area of the graph representing an extended period of time, such as depicted in FIG. 3, by the extension of various curves thereshown beyond the testing period. The projected service life of the silicon nitride article is determined from the projected curve. As mentioned before, the samples having curves similar to or below the curve identified by numeral I in FIG. 3 would be silicon nitride articles having an acceptable life of X hours, whereas those falling above the curves would be unacceptable.

The point A and the X hours required for service life, of course, may be shifted back and forth along the X dimension of the graph as desired by the service life required in various turbine engine components for example. Those articles which are easy to change, may need only a limited service life with the requirement that the articles be changed on specified intervals. More difficult articles to change, or those subjected to higher stresses, may require greater intervals of time between changes.

While a particular embodiment of this invention has been illustrated and described, it will be obvious to those skilled in the art that various changes and modifications may be made without departing from the invention, and it is intended to cover in the appended claims all such modifications and equivalents as fall within the true spirit and scope of this invention.

What is claimed is:

1. A method of selecting a newly manufactured silicon nitride article for use under high temperature oxidizing conditions which comprises:

determining the weight gain of a silicon nitride article under oxidizing conditions for a testing period of at least 12 hours at a temperature in the range from about 1800° F. (932° C.) to about 2500° F. (1371° C.);

empirically determining from the weight gain determinations made in said testing period the weight the silicon nitride article would gain at a projected time which is a number of hours greater than said testing period; and accepting or rejecting the silicon nitride article for further use under high temperature oxidizing conditions based upon the empirically determined weight gain at said projected time.

2. A method of predicting the service life of a silicon nitride article which comprises:

forming a silicon nitride article;

weighing said silicon nitride article to obtain its initial weight;

heating said silicon nitride article in an oxidizing ambient to an aging temperature in the range from about 1800° F. (932° C.) to about 2500° F. (1371° C.);

maintaining said silicon nitride article at said aging temperature a total of at least 12 hours to establish a testing period;

cooling said silicon nitride article back to room temperature (a) at least twice during the period of time over which said testing period is being established, and (b) also at the end of said testing period;

weighing said silicon nitride article each time it is cooled back to room temperature to obtain the weight gained by said silicon nitride article;

plotting a function of said weight gain of said silicon nitride article versus a function of the amount of time elapsed in said testing period at which the weight gain was measured;

fitting a curve through said plotted data;

extrapolating said curve into an area of said graph representing an extended period of time; and determining the projecting service life of the silicon nitride article from said extrapolated curve.

3. The method of claim 2, wherein said testing period is a period of 16 hours and said silicon nitride article is cooled back to room temperature at the end of the fifth and the tenth hour of said testing period.

4. The method of claim 2 or claim 3, in which the function of weight gain plotted is percent by weight weight gain and the function of time period plotted is elapsed hours of testing.

* * * * *